United States Patent
Farrell et al.

(10) Patent No.: US 6,506,163 B1
(45) Date of Patent: Jan. 14, 2003

(54) METHOD AND SYSTEM OF DISTINGUISHING PRESSURE PULSES FROM V WAVES DURING WEDGE PRESSURE MEASUREMENT

(75) Inventors: Robert M. Farrell, Brown Deer, WI (US); Michael W. Jopling, Columbus, OH (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 109 days.

(21) Appl. No.: 09/723,714

(22) Filed: Nov. 28, 2000

(51) Int. Cl.[7] .................................................. A61B 5/02
(52) U.S. Cl. ....................... 600/486; 600/500; 600/508; 600/513
(58) Field of Search ................................ 600/485, 486, 600/508, 513, 500

(56) References Cited

U.S. PATENT DOCUMENTS 6,067,466 A * 5/2000 Selker et al. ................ 600/513
6,238,349 B1 * 5/2001 Hickey ........................ 600/486
6,405,076 B1 * 6/2002 Taylor et al. ................ 600/513

OTHER PUBLICATIONS

Gloria Oblouk Darovic, Hemodynamic Monitoring: Invasive and Noninvasive Clinical Application, Second Edition, W.B. Saunders Company, 1995, 5 pages.

L.A. Eidelman, Pulmonary Artery Catheterization–At The Crossroads, Critical Care Medicine, vol. 22 No. 4, pp. 543–545, Apr. 1994.

O.C. Kirton et al., Flow–Directed, Pulmonary Artery Catheter–Induced Pseuodoaneurysm: Urgent Diagnosis and Endovascular Obliteration, Critical Care Medicine, vol. 20 No. 8 pp. 1178–1180, Aug.1992.

* cited by examiner

*Primary Examiner*—Willis R. Wolfe
*Assistant Examiner*—Johnny H. Hoang
(74) *Attorney, Agent, or Firm*—Michael Best & Friedrich LLP

(57) ABSTRACT

A method and system of distinguishing physiological pulses as measured by pulmonary artery catheterization. The method includes positioning two measurement devices in blood vessels of a subject, one in a major systemic artery and one in the pulmonary artery, and measuring blood pressure in the blood vessel with the measuring device to generate a pressure waveform. A phase difference between the two pressure waveforms is determined and used to create a warning or to display the phase difference on a display. The system includes an analysis module that determines phase differences based on the inputs from two or more physiological sensing modules.

28 Claims, 3 Drawing Sheets

METHOD AND SYSTEM OF DISTINGUISHING PRESSURE PULSES FROM V WAVES DURING WEDGE PRESSURE MEASUREMENT

BACKGROUND OF THE INVENTION

The present invention relates to methods and devices used to measure and record physiological data, such as blood pressure and electrocardiogram data. More particularly, the invention relates to a method and a system of distinguishing pressure pulses to avoid potential harm to patients while making physiological measurements.

Modem medical practice involves monitoring a variety of physiological data, including electrical activity and blood pressure. Electrocardiograms ("ECG") are used to measure electrical activity that controls the contraction of the heart. As is known, prominent parts of an ECG are the P wave, a deflection caused by the current originating in the atrium; the QRS complex, which represents the electrical activity of the ventricles as they contract; and the T wave, which denotes ventricular relaxation. These changes in electrical activity may, in general, be sensed using electrodes attached to the body.

The pulsatile pressure of blood in a large or "great" artery of the body (the "arterial pressure waveform") may be sensed by introducing a fluid-filled catheter into a major artery of the systemic circulation, such as the radial, brachial, or femoral artery, and connecting it to a pressure transducer. The arterial pressure waveform represents the mechanical activity of the heart, and therefore follows, or lags, the electrical activity. The upstroke of the pressure waveform follows the QRS complex of the ECG and is due to the contraction of the left ventricle as blood is forced into the aorta through the aortic valve. The peak of the pressure pulse is the peak systolic pressure. A small dip, called the dicrotic notch, caused by the closure of the aortic valve, may be observed on the downstroke of the pulse. The gradual decrease in pressure after the dicrotic notch is due to run-off of the blood to the peripheral arteries.

Blood pressure may also be monitored in other parts of the body. The pressure may be measured in the pulmonary artery though the use of a pulmonary artery catheter. In this case, the pulmonary artery catheter is introduced into the body through a major vein such as the femoral or subdlavian vein. It is threaded through the vena cava, the right atrium, the right ventricle, and rests in a branch of the pulmonary artery. At the distal tip of the pulmonary artery catheter is an opening to a fluid-filled lumen through which the pulmonary artery pressure is sensed. The appearance of the pulmonary artery pressure waveform is similar to the arterial pressure waveform described above, although the pressures are about one sixth the value of the pressures in the major arteries. The pressure pulse is created as blood flows through the pulmonary valve due to right ventricular contraction followed by run-off into the pulmonary circulation. Pulmonary artery catheterization is a very invasive procedure with many associated risks. The procedure is generally used in circumstances where a patient has a severe medical condition that requires intensive care and observation.

One measurement that may be made with the pulmonary artery catheter in place is the pulmonary artery wedge pressure ("PAWP"). In this measurement, a balloon near the end of the catheter is inflated, occluding flow through that branch of the pulmonary circulation. (The balloon is said to be "wedged" in the pulmonary artery.) The stagnant blood at the distal tip of the catheter is, in effect, at the same pressure as the blood in the left atrium, which, when the mitral valve is open, is also at the same pressure as the blood in the left ventricle. One hazard associated with the pulmonary artery wedge pressure measurement is that the catheter balloon may be over-inflated by the clinician, resulting in a tear or rupture of the pulmonary artery. As should be apparent, a rupture of the pulmonary artery can have dire consequences for the patient.

During the PAWP measurement, the pulmonary artery waveform takes on a dampened appearance, as the pressure waveform represents the left atrial pressure rather than the pulsatile pulmonary artery pressure. Prominent parts of the PAWP waveform may be identified and correlated to the ECG. An a wave is produced by left atrial contraction and follows the P wave of the ECG. The descending portion of the a wave is called the x-descent, reflecting left atrial relaxation. A small positive deflection is sometimes visible on the x-descent. This deflection, called the c wave, is produced by the closure of the mitral valve. The v wave is produced by the filling of the left atrium against the closed mitral valve during ventricular systole and, therefore, occurs after the R wave of the ECG (more precisely, it occurs after the T wave of the ECG). The downstroke following the peak of the v wave is termed the y-descent, which represents the opening of the mitral valve and a decrease in left atrial pressure and volume during passive emptying into the left ventricle.

The v wave of the PAWP waveform is exaggerated and elevated in patients with mitral insufficiency as the mitral valve does not completely close during the ventricular contraction, causing a regurgitation of blood back into the left atrium. This condition is commonly referred to as mitral valve regurgitation (MVR). PAWP measurements can become more difficult to take in this case because the large v waves may resemble the unwedged pulmonary artery pressure pulse and lead the unwary clinician to believe that the catheter has not properly wedged in the pulmonary artery. This can result in repeated attempts to wedge the catheter (with the risk of PA rupture or perforation). Conversely, it may result in prolonged wedging if the clinician erroneously believes the catheter is in the unwedged state and goes about his duties (with the risk of pulmonary infarction).

It is believed that a major cause of balloon over-inflation and subsequent pulmonary artery rupture during PAWP measurements is a failure by the clinician to recognize and differentiate between large v waves and pulmonary artery pressure pulses on pressure tracings, which are typically presented electronically on a monitor or similar display.

SUMMARY OF THE INVENTION

Accordingly, it would be desirable to have a method and system for differentiating between pressure pulses due to right ventricular contraction and v waves during the PAWP measurement. The invention provides a method and a system for differentiating between regular pulmonary artery pressure pulses and v waves sensed during a PAWP measurement. The method involves computing or determining the timing or the phase delay between the peak of a PA pressure pulse and the peak of the corresponding arterial pressure pulse. The method also involves observing a change in the phase or timing between the arterial pressure and the PA pressure pulses.

Typically, the arterial and PA pressure pulses occur almost simultaneously. However, v waves occur later in the cardiac cycle than the regular pressure pulse peak. The inventors have observed that a change of timing or phase delay between the arterial pulse peak and the observed peak of the PA waveform indicates that a wedge is in place and that large v waves have been detected. Thus, the invention further includes an indication of a phase change between the arterial and PA pressure peaks, such as a plot of the phase difference over time. The inventors have observed that such as plot yields readily identifiable balloon inflation and deflation times in the form of step responses.

The method involves using a reference signal for timing. In one embodiment of the invention, the PA peak pressure time may be measured with respect to the R wave of an ECG waveform. In another embodiment of the invention, the PA peak pressure time is measured with respect to the peak pressure of an arterial pressure signal. Other reference waveforms, including plethysmograms, may also be used. Preferably, a combination of ECG and arterial pressure timings are used.

The peak PA pressure is monitored and stored on a beat-by-beat basis, and the phase measurement is calculated in a processor of a monitoring system. The monitor alerts the clinician that a wedge is in place and that further inflation should not occur. In addition to notifying the clinician of a wedged balloon during intentional PAWP measurements, the invention may also be used to alert a clinician that a spontaneous (unintentional) wedge has occurred during normal PA monitoring.

As is apparent from the above, it is an advantage of the present invention to provide a method and system of differentiating between regular pressure pulses and v waves measured during patient monitoring. Other features and advantages of the present invention will become apparent by consideration of the detailed description and accompanying drawings.

DETAILED DESCRIPTION

Figure 1:
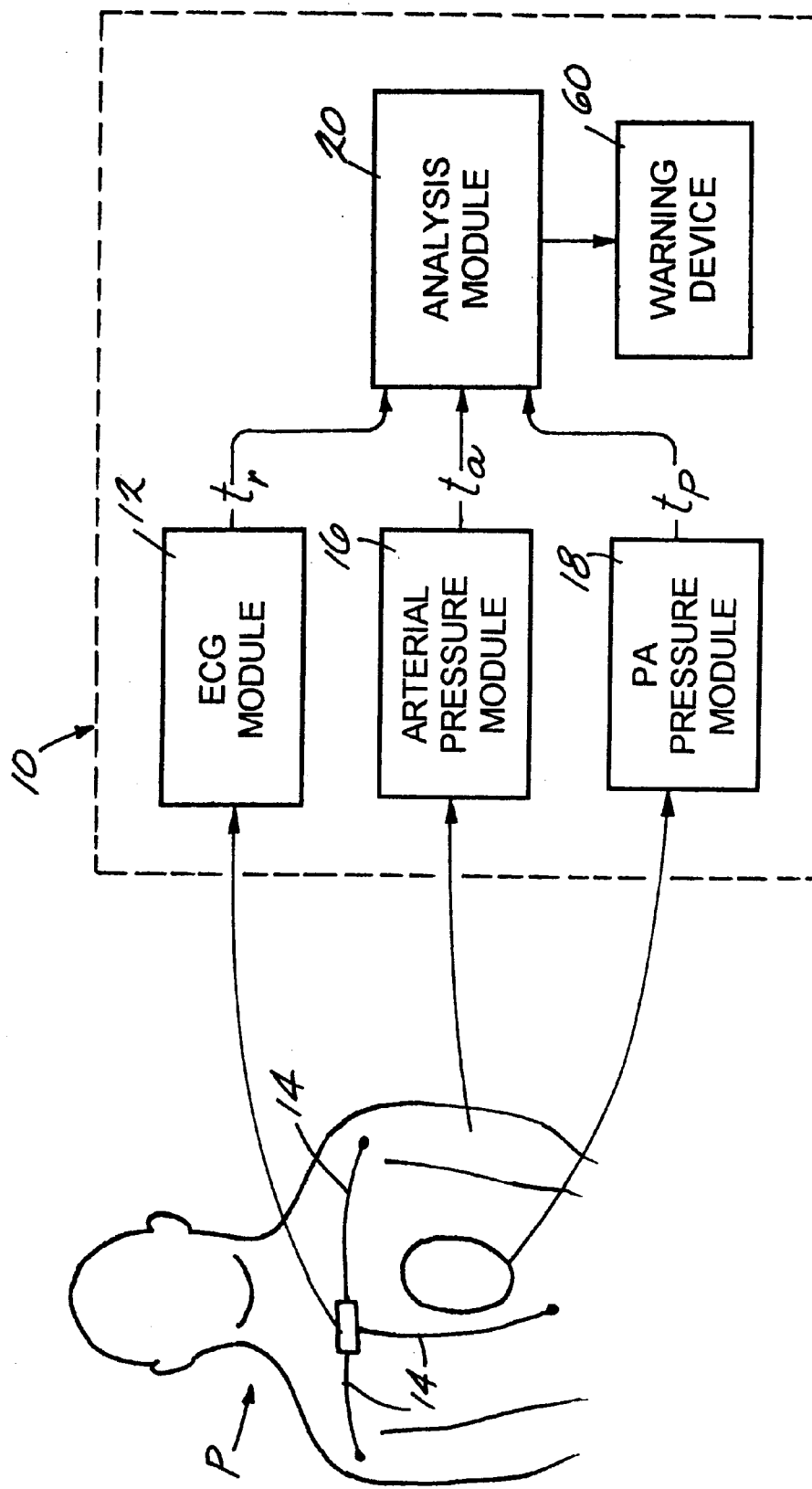
FIG. 1 is a schematic drawing of an apparatus embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates an apparatus or acquisition module 10 for acquiring ECG and invasive pressure waveforms that embodies the invention. While this apparatus is shown as a single unit, the apparatus may be separated into discrete components that operate generally independent of the others. This apparatus includes an ECG module 12 that, in the usual application, is externally connected to the patient through leadwires and electrodes 14 attached to the skin of a patient P. The invention, however, is equally applicable to ECGs that are acquired in other ways, e.g., through electrodes placed directly on the heart, through transesophageal monitoring, etc.

The acquisition module 10 also includes an arterial pressure waveform module 16. The module 16 is connected to a pressure sensor, such as an invasive sensor, although other sensors capable of providing pulsatile pressure measurements may be used. The acquisition module 10 also includes a second blood pressure module 18, for the measurement of the PA pressure. The module 18 is connected to a sensor or transducer on a catheter situated in the pulmonary artery.

Data from the modules 12, 16, and 18 is analyzed in an analysis module 20. The analysis module 20 includes analysis software (explained in greater detail below) that provides a means for identifying the phase difference between arterial pressure and pulmonary artery waveforms using an ECG waveform as a reference.

Figure 2:
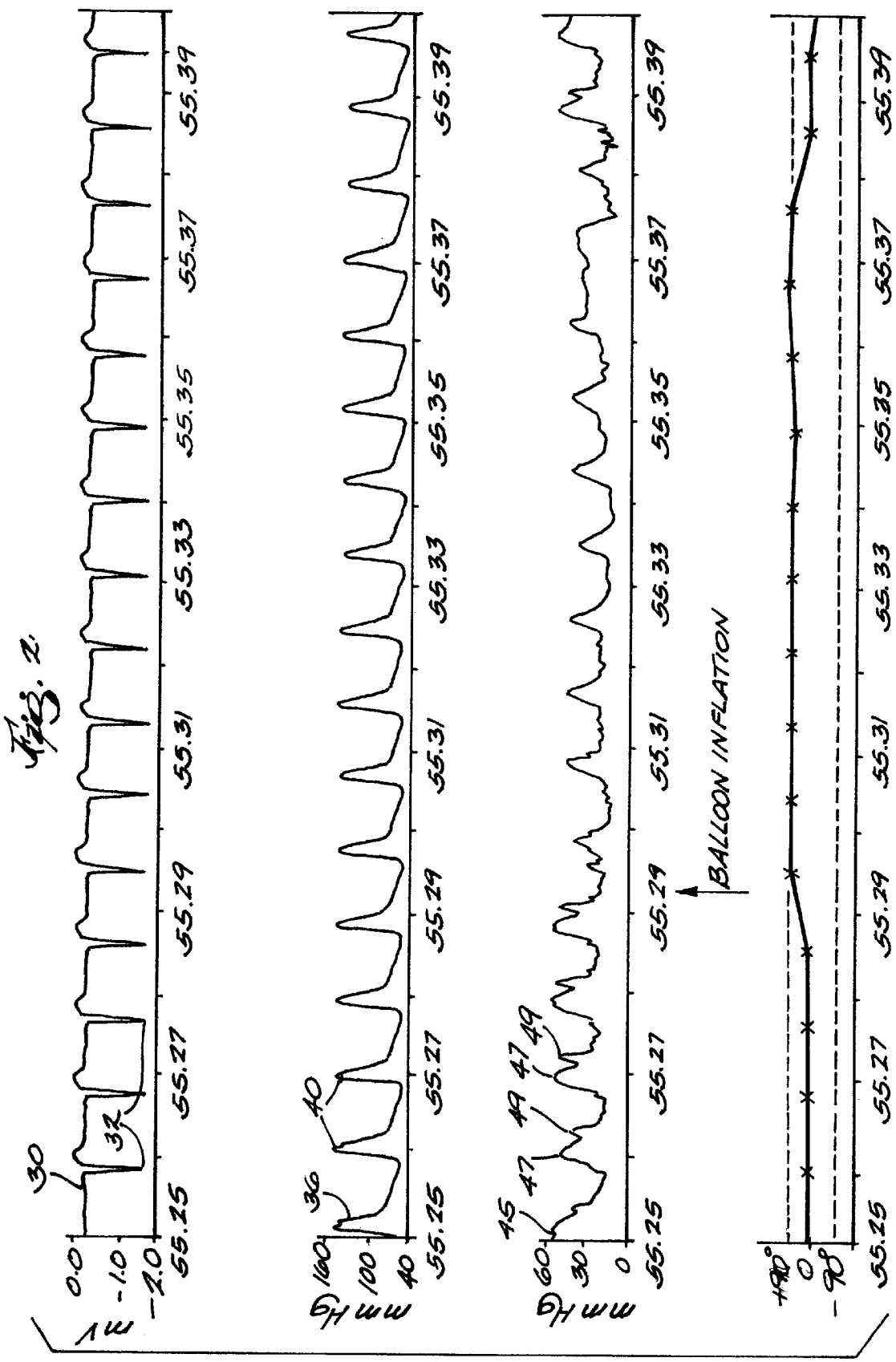
FIG. 2 is a waveform diagram illustrating a reference ECG wave, an arterial pressure waveform, a pulmonary artery pressure waveform from a PAWP measurement, and a plot of the phase difference between the peaks of arterial and PA pressure pulse measurements.

FIG. 2 illustrates three exemplary waveforms and a plot of the phase difference between two of those waveforms. The first waveform is an ECG waveform 30 with repeating QRS complexes 32. The second waveform is an arterial pressure waveform 36 with repeating pulses 40. The third waveform is a PA pressure waveform 45 with regular, right ventricular pressure pulses 47 and v waves 49. The fourth waveform shows the phase difference between the peaks of the arterial pressure pulses of waveform 36 and the PA pressure pulses of waveform 45 using the ECG waveform 30 as a reference. Under normal conditions the phase difference between the peak associated with each beat in waveforms 36 and 45 is zero or near zero. When a wedge condition exists, i.e., a catheter is blocking a branch of the pulmonary artery, the phase difference reaches about 90°. When the blockage is removed, the phase difference returns to zero.

The invention provides real-time integration of information from multiple input signal sources (i.e., ECG, arterial pressure, and PA pressure) to support its decision-making. The integration and analysis of this information is best explained by reference to FIGS. 1 and 3.

Figure 3:
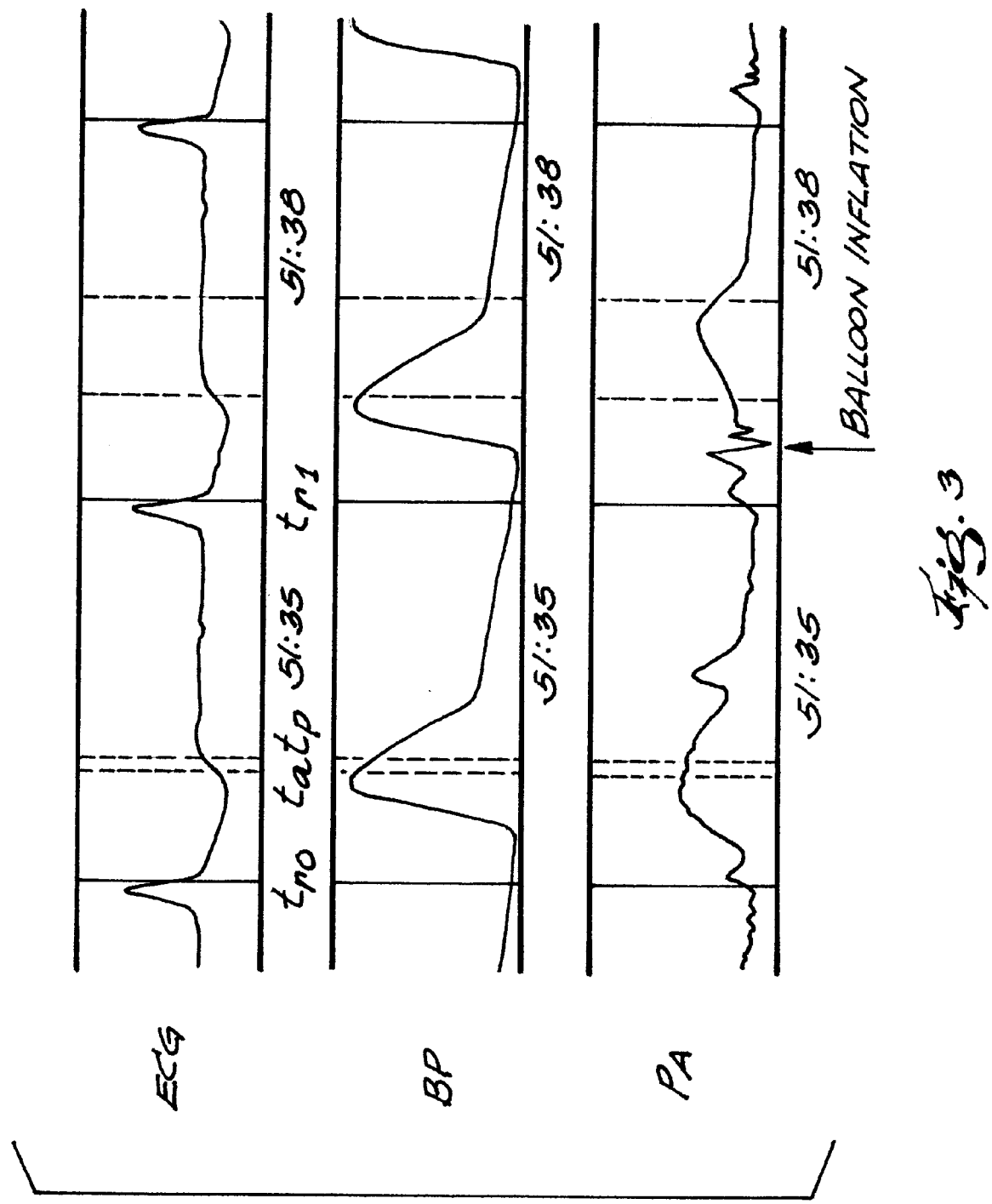
FIG. 3 is a waveform diagram illustrating an ECG wave, an arterial pressure wave, and a pulmonary artery pressure wave with time-marked events used in the algorithm implemented by the invention.

As shown, the analysis module 20 receives inputs from the ECG module 12, the arterial pressure module 16, and the PA pressure module 18. In FIG. 3, time $t_{r0}$ corresponds to the peak of the R wave of the first QRS complex. Time $t_{r1}$ corresponds to the R wave of the second QRS complex. Time $t_a$ corresponds to the peak of the arterial pressure pulse. A time difference, $t_{ar}$, is then computed according to:

$$t_{ar} = t_a - t_{r0} \quad \text{(eqn. 1)}.$$

The peak arterial pressure, $P_a$, is then stored. If another arterial pulse is detected before time $t_{r1}$, the pulse with the greatest peak pressure (Pa) is deemed to be the true pulse and the time that that pulse occurred is used as the time $t_p$.

At time $t_p$, the PA pressure module detects the peak of the pulmonary artery pressure pulse. This pressure pulse may actually be a v wave. A time difference, $t_{pr}$, between the peak PA pressure pulse and the first R wave is then calculated according to:

$$t_{pr} = t_p - t_0 \quad \text{(eqn. 2)}.$$

The peak arterial pressure $P_p$ is then stored. If another PA pulse is detected before $t_{r1}$, then the pulse with the greatest peak pressure ($P_p$) is deemed to be the true pulse and the time of its occurrence is used as the time $t_p$.

When the next R wave is detected from the ECG module, the time difference, $t_{rr}$, between the two R waves is then calculated according to:

$$t_{rr}=t_{r1}-t_{r0} \quad \text{(eqn. 3)}.$$

The phase differences between the first R wave of the ECG waveform and the arterial and PA peaks, respectively, are then calculated according to:

$$\phi_a=360*(t_a-t_{r0})/t_{rr} \quad \text{(eqn. 4) and}$$

$$\phi_p=360*(t_p-t_0)/t_{rr} \quad \text{(eqn. 5)}.$$

Then a difference, $\phi_{pa}$, between the two phases $\phi_a$ and $\phi_p$ is calculated according to $\phi_{pa}=\phi_p-\phi_a$(eqn. 6), where $\phi$ denotes an angular phase difference measured in degrees.

If no arterial or PA pressure pulse is detected between $t_{r0}$ and $t_{r1}$, then no time or phase difference can be computed for that heartbeat. This happens, for example, during a wedge pressure measurement of a patient that does not exhibit large v waves (i.e., does not have mitral valve regurgitation (MVR)). Once the phase difference between the arterial and PA pressure peaks is computed, a determination can be made as to whether the PA pressure pulse was due to a right ventricular pressure pulse (the normal, un-wedged, condition), or to a reflected v wave (as would be observed in a patient with (MVR) during a wedge). Patients without MVR usually do not exhibit pulsations in the PA waveform during a wedge.

In the normal unwedged state, a phase difference near zero is expected. If the phase difference suddenly increases to about 90 degrees (a step response), it can be concluded that the catheter balloon is inflated and that the patient exhibits large v waves. To warn the clinician of this condition, the analysis module generates an output signal that can be delivered to a warning device 60 (FIG. 1) such as an audible or visible warning mechanism. Activation of the warning device indicates that the pulses observed on the PA waveform are from v waves, that the balloon is in the wedged state, and that the clinician should not attempt to further inflate the balloon. Alternatively, a phase waveform, such as the one shown in FIG. 2 may be output to a display to be viewed by a clinician. Upon seeing a step response, the technician would recognize a wedged state.

The algorithm described above does not require fixed thresholds for discrimination of normal, non-wedged peaks and v wave peaks (i.e., the 0 and 90 degree values mentioned above). Rather, the invention can operate using a steady state value and trigger a warning only if the phase difference changes significantly from the steady state value. As an optional feature, the algorithm may be modified with an alarm filter such that a warning signal is not generated unless the increased phase difference occurs for a threshold period, such as 2 consecutive heartbeats.

The algorithm described above computes the phase difference between peaks as the unit of measure. The phase difference is merely the time difference between peaks normalized by the beat duration, and multiplied by 360 so that the measure is in units of degrees. However, the invention may simply use the time duration between peaks.

The algorithm described above assumes the presence of ECG, arterial BP, and PA pressure signals. (In most real world cases, a patient with PA monitoring will have ECG and arterial pressure monitoring.) However, the invention could be modified to work with PA pressure and only one of either the ECG or arterial pressure. In addition, other physiological activity waveforms, such as A plethysmograms, may also be used as reference waveforms.

In the case of ECG and PA pressure, the algorithm computes only the time and phase differences between the R wave and the PA pulse peak and looks for an increased phase difference from the steady state value. In the case of arterial pressure and PA pressure, the algorithm computes only the time and phase differences between the respective pressure peaks and looks for an increased phase difference from the steady state value. In place of $t_{rr}$ (the duration of one beat, as measured from R wave to R wave), another beat duration measure could be used, such as the time between two consecutive arterial pressure peaks.

Nevertheless, the use of all three signals improves the sensitivity and specificity of the method. Further, based on present technology, the ECG signal is the preferred reference signal.

In addition to the applications and advantages noted, the invention can be used to detect PA catheter migration. It is possible for a catheter to migrate distally into the pulmonary circulation system on its own (i.e., not during a wedge measurement). When this occurs, the catheter blocks pulmonary circulation. The blocked circulation is detected, in the same manner a wedge is detected, and a warning is made, allowing the clinician to remove the catheter before a pulmonary infarction or other damage occurs.

As can be seen from the above, the invention provides a method and system for differentiating between regular PA pressure pulses and v waves in the pulmonary artery during PAWP measurement, and of notifying the user of the placement of a wedge when it might have otherwise gone undetected.

Various features and advantages of the invention are set forth in the following claims.

What is claimed is:

1. A method of distinguishing between right ventricular pressure pulses and v waves acquired from a subject, the method comprising:

positioning a measurement device in a blood vessel of the subject;

measuring blood pressure in the blood vessel with the measurement device to render a pressure waveform;

positioning a second measurement device on the subject;

measuring a physiologic activity with the second measurement device to render a reference waveform;

calculating a phase difference between the pressure waveform and the reference waveform; and generating information based on the phase difference.

2. A method as claimed in claim 1, wherein the act of positioning a measurement device in a blood vessel includes the act of introducing a pulmonary artery catheter into a pulmonary artery of the body.

3. A method as claimed in claim 2, wherein the act of measuring blood pressure in the blood vessel includes measuring pulmonary artery blood pressure.

4. A method as claimed in claim 3, further comprising measuring electric activity of the heart to detect at least one R wave of an ECG waveform.

5. A method as claimed in claim 4, wherein the pulmonary artery blood pressure is measured with respect to the at least one R wave.

6. A method as claimed in claim 3, wherein the act of positioning a second measurement device on the subject includes positioning a device capable of measuring a pulsatile pressure on the patient.

7. A method as claimed in claim 6, wherein the act of measuring an activity includes measuring an arterial blood pressure.

8. A method as claimed in claim 7, wherein the act of calculating a phase difference includes measuring a pulmonary artery peak pressure and an arterial peak pressure.

9. A method as claimed in claim 8, wherein the pulmonary artery peak pressure is measured with respect to an R wave of an ECG waveform.

10. A method as claimed in claim 8, wherein the pulmonary artery peak pressure is measured with respect to a peak pressure of an arterial pressure signal.

11. A method as claimed in 8, wherein the pulmonary artery peak pressure is measured with respect to an R wave of an ECG waveform and a peak pressure of an arterial pressure signal.

12. A method as claimed in claim 1, wherein generating information based on the phase difference includes displaying a phase difference waveform on a display device.

13. A method as claimed in claim 1, wherein generating information based on the phase difference includes generating a warning signal.

14. A method of differentiating pressure pulses from v waves in the pulmonary artery of a subject, the method comprising:
 positioning a catheter in a pulmonary artery of the subject;
 measuring pulmonary artery pressure pulses in the pulmonary artery with the catheter by generating a pulmonary artery blood pressure waveform;
 positioning a pressure sensor on the subject;
 measuring at least one arterial pressure pulse with the pressure sensor by generating an arterial pressure waveform;
 calculating a phase difference between the pulmonary artery pressure waveform and the arterial pressure waveform; and
 displaying information based on the phase difference on a display device.

15. A method as claimed in claim 14, further comprising measuring electric activity of the heart to detect at least one R wave of an ECG waveform.

16. A method as claimed in claim 15, wherein the pulmonary artery blood pressure is measured with respect to the at least one R wave.

17. A method as claimed in claim 14, wherein the act of calculating a phase difference includes measuring a pulmonary artery peak pressure and an arterial peak pressure.

18. A method as claimed in claim 17, wherein the pulmonary artery peak pressure is measured with respect to an R wave of an ECG waveform.

19. A method as claimed in claim 17, wherein the pulmonary artery peak pressure is measured with respect to a peak pressure of an arterial pressure signal.

20. A system for distinguishing physiological activity pulses, the system comprising;
 a physiological activity detection module capable of determining the times of reference events of a reference activity;
 a pressure pulse detection module capable of determining the time of a pressure pulse of a pressure activity; and
 an analyses module that receives inputs from the physiological activity and pressure pulse detection modules, determines the phase difference between the reference activity and the pressure activity, and generates an output when the phase difference exceeds a threshold.

21. A system as claimed in claim 20, further comprising a second physiological activity detection module capable of determining the times of physiological events of a second physiological activity, wherein the analysis module receives an input from the second physiological activity and determines the phase difference between the pressure activity and the second physiological activity.

22. A system for distinguishing physiological activity pulses, the system comprising;
 a first physiological activity detection module capable of determining the times of pulses of a first physiological activity;
 a second physiological activity detection module capable of determining the times of pulses of a second physiological activity; and
 an analyses module that receives inputs from the first and second physiological activity modules, determines the phase difference between the first and second physiological activities, and generates an output when the phase difference exceeds a threshold.

23. A method for distinguishing physiological activity measurements, the method comprising:
 acquiring a pulmonary artery waveform;
 acquiring at least one other physiological waveform;
 comparing the pulmonary artery waveform and the at least one other physiological waveform; and
 calculating a temporal difference measure between the pulmonary artery waveform and the at least one other physiological waveform.

24. A method as claimed in claim 23, wherein the at least one other physiological waveform is an arterial blood pressure waveform.

25. A method as claimed in claim 23, wherein the at least one other physiological waveform is an ECG waveform.

26. A method as claimed in claim 23, wherein the at least one other physiological waveform is a plethysmogram waveform.

27. A method as claimed in claim 23, wherein the temporal difference measure is time.

28. A method as claimed in claim 23, wherein the temporal difference measure is phase.

* * * * *